United States Patent [19]

Yoshida et al.

[11] 4,268,447

[45] May 19, 1981

[54] PROCESS FOR PRODUCING TETRAHYDROFURAN AND 1,4-BUTANEDIOL

[75] Inventors: Yoshinori Yoshida, Yokohama; Hiroshi Oka, Tokyo, both of Japan

[73] Assignee: Japan Synthetic Rubber Co., Ltd., Tokyo, Japan

[21] Appl. No.: 102,658

[22] Filed: Dec. 12, 1979

[30] Foreign Application Priority Data

Dec. 12, 1978 [JP] Japan .................................. 53/152724

[51] Int. Cl.³ ...................... C07D 307/08; C07C 31/20
[52] U.S. Cl. ................................ 260/346.11; 568/858
[58] Field of Search .................... 260/346.11; 568/858

[56] References Cited

U.S. PATENT DOCUMENTS 4,156,685  5/1979  Tanabe et al. .................. 260/346.11

FOREIGN PATENT DOCUMENTS 53-87305  8/1978  Japan.

*Primary Examiner*—Henry R. Jiles
*Assistant Examiner*—Bernard Dentz

*Attorney, Agent, or Firm*—Oblon, Fisher, Spivak, McClelland & Maier

[57] ABSTRACT

A process for producing simultaneously tetrahydrofuran and 1,4-butanediol in any desired proportion which comprises (a) reacting the acetic ester of 1,4-butanediol with a theoretical or smaller quantity, based on said acetic ester, of water (preferably 0.2–0.8 mole of water per mole of said acetic ester) in the presence of an acidic catalyst, (b) distilling, in the first distillation column, the reaction mixture to separate it into a distillate comprising tetrahydrofuran as major constituent and a bottom stream comprising as major constituent the acetic ester of 1,4-butanediol and (c) subjecting, in the second reaction-distillation column, at least a part of said bottom stream to a counter-current gas-liquid contact reaction with methanol, the quantity of said methanol being preferably 1–5 moles per mole of the acetate group of the acetic ester, in the presence of an acidic or basic catalyst and, simultaneously therewith, separating the reaction mixture into a bottom stream comprising 1,4-butanediol as major constituent and a distillate comprising methyl acetate as major constituent. By this process, methanol and catalyst can be economized to a great extent.

15 Claims, 1 Drawing Figure

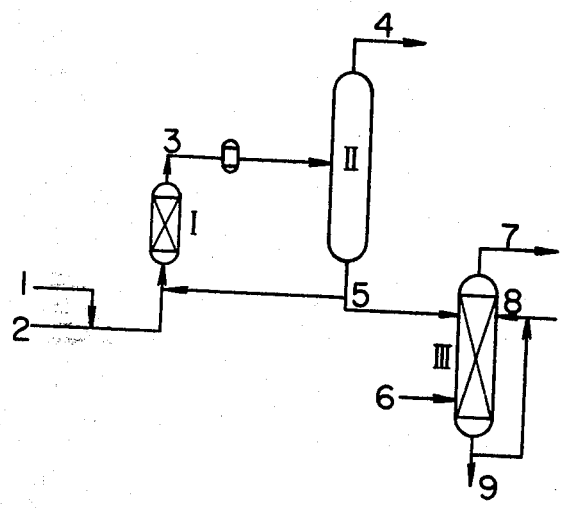

PROCESS FOR PRODUCING TETRAHYDROFURAN AND 1,4-BUTANEDIOL

This invention relates to a process for producing simultaneously tetrahydrofuran and 1,4-butanediol from the acetic ester of 1,4-butanediol. More particularly, this invention relates to a process for producing simultaneously tetrahydrofuran and 1,4-butanediol in any desired proportion which comprises reacting the acetic ester of 1,4-butanediol with a theoretical or smaller quantity, based on the acetic ester, of water in the presence of an acidic catalyst, distilling the reaction mixture to take out tetrahydrofuran as a distillate, subjecting the unreacted di-acetic ester and the formed mono-acetic ester withdrawn as a bottom stream to transesterification with methanol in the presence of an acidic or basic catalyst, and distilling the reaction mixture to obtain 1,4-butanediol.

Tetrahydrofuran and 1,4-butanediol are both quite useful as organic solvents or as the starting materials for the production of high polymers, and they are manufactured by various processes. For example, it is known that tetrahydrofuran can be produced by the hydrogenation of furan obtained by decarbonylating furfural, or by the dehydrating cyclization of 1,4-butanediol obtainable by hydrogenating either butinediol which can be produced from acetylene and formaldehyde or 2-butene-1,4-diol which can be derived from 1,4-dichlorobutene, or by the hydrogenation of maleic anhydride, or by reacting the acetic ester of 1,4-butanediol with water in the presence of an acidic catalyst. It is also known that 1,4-butanediol can be produced by the hydrogenation of butinediol, or by the hydrolysis of the acetic ester of 1,4-butanediol, or by transesterification reaction of the acetic ester of 1,4-butanediol.

As to the simultaneous production of tetrahydrofuran and 1,4-butanediol, a process for producing tetrahydrofuran in any desired proportion by the dehydrating cyclization of a part of the 1,4-butanediol obtained by various methods, and a process for producing tetrahydrofuran and 1,4-butanediol in any desired proportion by controlling the amount of water used, the reaction temperature and the residence time in hydrolyzing the acetic ester of 1,4-butanediol, particularly 1,4-diacetoxybutane, have been disclosed hitherto. In the simultaneous production process in which tetrahydrofuran is produced via 1,4-butanediol, however, there is a fatal economical defect that the cost of tetrahydrofuran becomes higher than the value obtainable by multiplying the cost of 1,4-butanediol by the inverse ratio of molecular weight. In the process by which tetrahydrofuran and 1,4-butanediol are simultaneously produced by hydrolyzing 1,4-diacetoxybutane, there is a fault that, as mentioned in Japanese Patent Application Kokai (Laid-Open) No. 87,305/78, for example, the equilibrium constant of the hydrolysis reaction regarding 1,4-butanediol is so small that the amount of water used becomes very large which requires a great thermal load on the subsequent separation of water by distillation.

The present inventors have conducted extensive research on the process for producing simultaneously tetrahydrofuran and 1,4-butanediol with an industrial advantage from 1,4-diacetoxybutane which is the di-acetic ester of 1,4-butanediol. As a result, it has been found, entirely different from the aforementioned case of Japanese Patent Application Kokai (Laid-Open) No. 87,305/78, that tetrahydrofuran can be obtained with a greatly enhanced conversion of water if the cyclization reaction is carried out by using water in an amount not larger than the theoretical quantity based on 1,4-diacetoxybutane, that 1,4-butanediol can be obtained in a quantitative yield by subjecting the residual liquid (mainly comprising the unreacted acetic ester) obtained by separating tetrahydrofuran from the reaction mixture to subsequent transesterification with methanol, that the amount of methanol as well as the amount of catalyst used in this case can be made smaller than those used in the direct transesterification of 1,4-diacetoxybutane because the residual liquid comprising mainly the unreacted acetic ester, to be subjected to the transesterification, contains 1-hydroxy-4-acetoxybutane formed by partial hydrolysis and 1,4-butanediol formed by the hydrolysis of both molecular ends, and that tetrahydrofuran and 1,4-butanediol can be produced in any desired proportion by selecting the amount of unreacted acetic ester to be subjected to the transesterification depending upon the desired yield of 1,4-butanediol and recycling the residual portion to the cyclization reaction.

Thus, it is an object of this invention to provide a process for producing tetrahydrofuran and 1,4-butanediol simultaneously in any desired proportion from the di-acetic ester of 1,4-butanediol.

It is another object of this invention to provide a process for the simultaneous production of tetrahydrofuran and 1,4-butanediol by which the amounts of methanol and catalyst can be economized to a great extent as compared with a conventional process for producing tetrahydrofuran and 1,4-butanediol independently from the di-acetic ester of 1,4-butanediol.

Other objects and advantages of this invention will become apparent from the following description.

According to this invention, there is provided a process for producing tetrahydrofuran and 1,4-butanediol simultaneously in any desired proportion which comprises (a) reacting the acetic ester of 1,4-butanediol with a theroretical or smaller quantity, based on said acetic ester, of water in the presence of an acidic catalyst, (b) separating the reaction mixture in the first distillation column into a distillate comprising tetrahydrofuran as major constituent and a bottom stream comprising the acetic ester of 1,4-butanediol as major constituent and (c) subjecting at least a part of said bottom stream to counter-current gas-liquid contact reaction with methanol in the presence of an acidic or basic catalyst in the second reaction-distillation column and separating the reaction mixture into a bottom stream comprising 1,4-butanediol as major constituent and a distillate comprising methyl acetate as major constituent.

The starting acetic ester of the diol used in this invention is specifically 1,4-diacetoxybutane, which may contain up to 50 mole% of mono-acetic esters of 1,4-butanediol, such as 1-hydroxy-4-acetoxybutane and the like. 1,4-Diacetoxybutane can be obtained by hydrogenating, for example, 1,4-diacetoxybutene-2 synthesized by subjecting butadiene, acetic acid and oxygen to reaction in the presence of a palladium catalyst. Though water, i.e. the other starting material for the cyclization reaction, is not particularly restricted, it preferably contains no corrosive ions. The amount of water used in the reaction should be theoretical or smaller, i.e. equimolar or less, based on the di-acetic ester, i.e. 1,4-diacetoxybutane, supplied to the cyclization reaction. Preferably, the water is used in an amount of 0.2–0.8 mole per mole of the di-ester. That the water is used in a theoretical or smaller amount is one of the characteristic features of this invention. If the amount of water used exceeds the equimolar quantity, the conversion of water drops and the amount of water introduced into the subsequent step in the unreacted state increases, so that much heat becomes required for the separation thereof by distillation. If the amount of water is less than 0.2 mole, one pass yield of tetrahydrofuran is too low and the amount of unreacted acetic ester to be recycled increases so that the volume of reactor and the amount of catalyst have to be increased, which is undesirable. Thus, an amount of water ranging from 0.2 mole to 0.8 mole is desirable in that the conversion of water is high and the amount of the unreacted acetic ester recycled does not become too large. As the acidic catalyst for the cyclization reaction, there may be mentioned liquid acids such as sulfuric acid, phosphoric acid and the like and solid acids such as acidic cation exchange resin, solid phosphoric acid, silica-alumina and the like, among which the acidic cation exchange resin can be used with advantage in general.

The shape and material for cyclization reactor may be varied depending on the kind of catalyst used. When an acidic cation exchange resin is used, a tubular packed reactor made of a material such as stainless steel of SUS 304 or SUS 316 grade or the like is used. When an acidic cation exchange resin is used, the reaction temperature is preferably 140° C. or less if the heat resistance of the resin is considered. However, too low a temperature results in a reduction in reaction efficiency, so that a temperature of 80°–130° C. is preferable. The residence time is defined by LHSV (liquid space velocity) and may be varied depending on reaction temperature. LHSV is selected in the range of 0.1–2.0 hr$^{-1}$ and preferably in the range of 0.2–1.0 hr$^{-1}$.

The first distillation column may be of the same type as usually employed distillation columns, and a multi-plate distillation column or a packed distillation column may be used. Its material is preferably a stainless steel of SUS 316 grade because acetic acid formed by the cyclization reaction is distilled there. Usually, the number of theoretical plates is about 5–30, the operation pressure is 50–760 Torr, preferably 100–500 Torr, and the reflux ratio is 0.1–3.

The distillate from the top of the first column is a liquid which contains tetrahydrofuran as main constituent and also contains water and acetic acid. By a refining this distillate is further purified by distillation to be separated into a fraction comprising tetrahydrofuran as major constituent and a fraction of acetic acid. The number of distillations and the extent of rectification may be freely selected in accordance with the desired purity of tetrahydrofuran.

The bottom stream of the first distillation column comprises unreacted acetic ester as major constituent, which is sent to the subsequent second reaction-distillation column, where it is subjected to transesterification. At this time, the bottom stream comprises not only the unreacted acetic ester but also 1-hydroxy-4-acetoxybutane formed by partial hydrolysis and 1,4-butanediol formed by hydrolysis of both molecular ends, so that the amount of methanol used can be made smaller than that in the direct transesterification of 1,4-diacetoxybutane. Though the degree of the decrease may be varied depending on the contents of 1-hydroxy-4-acetoxybutane and 1,4-butanediol, 10 to 30% of the methanol can be decreased usually. The methanol used in the transesterification may not necessarily be of high purity, but it may contain the methyl acetate formed as a by-product of the transesterification, provided that the allowable content of methyl acetate in methanol is 80 mole% or less, preferably 60 mole% or less. The amount of methanol used is 1.0–5.0 moles, particularly preferably 1.1–3.0 moles, per mole of the acetate group of the acetic ester of diol. When methyl acetate is contained in methanol, the mixture is used in such a manner that the amount of methanol in the mixture become the above-mentioned proportion. If the amount of methanol is less than 1.0 mole per mole of the acetate group, the transesterification does not proceed quantitatively. Use of more than 5.0 moles of methanol per mole of the acetate group is insignificant, and it is disadvantageous because it uselessly increases the amount of liquid and the thermal load.

The catalyst used in the transesterification includes liquid acids such as sulfuric acid, phosphoric acid and the like and solid acids such as acidic cation exchange resin, solid phosphoric acid, silica-alumina and the like as the acidic catalyst, and also sodium hydroxide, potassium hydroxide, sodium alkoxides, aluminum alkoxides, ammonia and the like as the basic catalyst, among which sodium hydroxide and potassium hydroxide are inexpensive and usually most advantageously used. The amount of the catalyst used may be varied depending on the kind thereof as well as on the proportions of 1-hydroxy-4-acetoxybutane and 1,4-butanediol contained in the bottom stream, so that it cannot be delt with uniquely. However, when sodium hydroxide is used as the catalyst, the amount of sodium hydroxide can be made 20–70% smaller than where a bottom stream comprising 1,4-diacetoxybutane alone is subjected to transesterification, because 1-hydroxy-4-acetoxybutane and 1,4-butanediol are present in the bottom stream. Though sodium hydroxide catalyst is advantageous from the industrial point of view, it can form, in some reactions, sodium acetate which is difficult to separate, so that how to decrease the amount of catalyst has been a problem. Now, owing to this invention, the amount of catalyst can be decreased to a great extent. If the concentration of sodium hydroxide catalyst is too low, the reaction velocity is low and the reaction stops on its way. If the concentration is too high, a useless salt is formed in a large quantity and its separation is difficult as mentioned above, which is undesirable. Therefore, it is usually preferable that the amount of sodium hydroxide catalyst used is 0.1–10 moles, more preferably 0.2–5 moles, per mole of the acetic ester of diol.

The reaction-distillation column for the transesterification may be of the same shape as generally used distillation columns, and a multi-plate distillation column or a packed distillation column may be used. Though its material may be varied depending on the kind of catalyst, a steel of SS 41 grade is enough for the purpose when a basic catalyst is used. In the case where an acidic catalyst is used, a stainless steel of SUS 304 grade or SUS 316 grade can be used and sometimes a glass-lined steel may be used. The number of theoretical plates is about 5–30. The operation pressure is not particularly restricted and may be normal pressure, though the operation can also be conducted under pressure, if necessary. The reflux ratio in the operation is usually in the range of 0–2. The reaction temperature is dependent on the temperature at the bottom of the column. If the bottom temperature of column is too high, there are formed by-products such as cyclic ethers, which is undesirable. If it is too low, the vapor of methanol cannot ascend, which is undesirable. Therefore, it should be in the range of 70°–180° C., more preferably in the range of 75°–150° C.

The distillate from the top of the second reaction-distillation column comprises methyl acetate as major constituent. When a basic catalyst is used, the bottom stream consists of 1,4-butanediol containing an alkali metal acetate.

Where not the whole but a part of the bottom stream of the first distillation column is supplied into the second reaction-distillation column to carry out the transesterification thereof with methanol, the residue of the bottom stream is recycled into the cyclization reactor as a starting material for the production of tetrahydrofuran. In this case, the bottom stream of the first distillation column is appropriately divided into the feed to the second reaction-distillation column and the recycle into the cyclization reactor in accordance with the most advantageous proportion in the simultaneous production of tetrahydrofuran and 1,4-butanediol. For example, when water is used in an amount of 0.5 mole per mole of 1,4-diacetoxybutane which is an acetic ester of diol, the one pass yield of tetrahydrofuran is about 35 mole%. If the whole quantity of the unreacted acetic ester is directly subjected to transesterification, 1,4-butanediol is obtained in a yield of about 65 mole%. Where tetrahydrofuran is to be produced in a proportion greater than 35 mole%, the amount of water used is increased in the range of up to 0.8 mole or the unreacted acetic ester is recycled in an amount corresponding to the desired yield. Where tetrahydrofuran is to be produced in a proportion smaller than 35 mole%, the amount of water used is made smaller than 0.5 mole. By such a procedure, tetrahydrofuran and 1,4-butanediol can be produced simultaneously in a substantially desired proportion.

This invention is explained with reference to the accompanying drawing, which is a flow sheet illustrating an embodiment of this invention, wherein:

I is a reactor,
II is a first distillation column,
III is a second reaction-distillation column,
1 is the feed line for water,
2 is the feed line for acetic ester,
3 is the discharge line for the cyclization mixture,
4 is the discharge line for tetrahydrofuran mixture,
5 is the outlet line for unreacted acetic ester,
6 is the feed line for methanol,
7 is the distilling line for methyl acetate mixture,
8 is the feed line for catalyst, and
9 is the outlet line for 1,4-butanediol mixture.

The acetic ester of a diol is fed through line 2 and a theoretical or smaller quantity, based on the acetic ester, of water is fed through line 1, both to the reactor I. They are reacted in the presence of an acidic catalyst and the resulting reaction mixture is fed to the first distillation column II through line 3. At this time, the reaction mixture may be neutralized by passing it through a bed of anion exchange resin, if necessary. The distillate comprising tetrahydrofuran as major constituent from the first distillation column, contains some water and acetic acid, from which distillate tetrahydrofuran can be obtained with high purity by combining subsequent distillations appropriately. On the other hand, the bottom stream of the first distillation column II comprising unreacted acetic ester as major constituent, is fed through line 5 to the upper part of the second reaction-distillation column III. By returning a part of the bottom stream, the production ratio of tetrahydrofuran to 1,4-butanediol can be controlled freely. In the second reaction-distillation column III, the bottom stream is subjected to a counter-current contact reaction with methanol which is fed from the lower part of the column through line 6. As the methanol source, it is allowable to use the methanol containing methyl acetate which can be obtained by partially hydrolyzing the methyl acetate by-product distilled out through line 7. The method of feeding the catalyst may be varied depending upon the kind of catalyst. When sodium hydroxide is used as the catalyst, it is dissolved in a part of the reaction mixture containing the diol or dissolved in methanol, and fed through line 8 to the upper part of the second reaction-distillation column III. After the reaction, a methanolic solution comprising 1,4-butanediol as major constituent but substantially free from unreacted acetic ester is obtained through line 9 as a bottom stream. From this mixture, 1,4-butanediol of high purity can be obtained by a simple distillation.

As mentioned above, in producing simultaneously tetrahydrofuran and 1,4-butanediol from the acetic ester of 1,4-butanediol, the process of this invention makes it possible to reduce the amount of water used to a great extent as compared with the case of hydrolyzing the acetic ester of 1,4-butanediol. Furthermore, the amounts of methanol and catalyst used can also be reduced because 1-hydroxy-4-acetoxybutane formed by the partial hydrolysis and 1,4-butanediol formed by the hydrolysis of both molecular ends are used in the transesterification, and the two products can be produced in any desired proportion. Therefore, the process of this invention is quite advantageous in industry.

This invention is illustrated more specifically below with reference to Examples and Comparative Example. The Example is by way of illustration and not by way of limitation.

EXAMPLE 1

A reactor made of a stainless steel of SUS 316 grade, having an inner diameter of 50 mm and a height of 700 mm and equipped with a heating jacket was used as cyclization reactor, the inner space of which was packed with 1,300 ml of a commercially available acidic cation exchange resin (trade mark Amberlite 200), converted to a sulfonic acid form by a treatment with hydrochloric acid, as a catalyst bed. As the first distillation column, a distillation column made of a stainless steel of SUS 316 grade, having an inner diameter of 25 mm and a height of 2,000 mm and equipped with a heating jacket was used, the inner space of which was packed with McMahon packings made of a stainless steel of SUS 316 grade and which was provided at the bottom with a 500-ml still equipped with a heating jacket. As the second reaction-distillation column, a distillation column made of a stainless steel of SUS 316 grade, having an inner diameter of 25 mm and a height of 1,500 mm and equipped with a heating jacket was used, the inner space of which was packed with McMahon packings made of a stainless steel of SUS 316 grade and which was provided at the bottom with a 500-ml still equipped with a heating jacket. After connecting the above-mentioned means through pumps, etc., a continuous reaction was carried out according to the accompanying drawing.

Water was fed through line 1 at a rate of 27 g/hr and 1,4-diacetoxybutane was fed through line 2 at a rate of 522 g/hr, both continuously and after being preheated to 120° C., to the reactor. The reaction mixture was taken out through line 3, passed through a tank packed with 130 ml of commercial anion exchange resin (trade name Amberlite IRA 400) treated with caustic soda, and then fed to the first distillation column. The first distillation column was continuously operated at a pressure of 200 Torr, at a column bottom temperature of 200° C. and at a reflux ratio of 0.5. The distillate was continuously taken out from line 4 at a rate of 217 g/hr, from which tetrahydrofuran having a purity of 99.9% or more was obtained at a rate of 75 g/hr by another combination of distillations.

On the other hand, the bottom stream (332 g/hr) withdrawn from the bottom of the first distillation column passed line 5 and was cooled to 100° C., after which it was fed to a position 100 mm below the top of the second reaction-distillation column. Methanol was fed to a position 400 mm above the bottom of the reaction-distillation column at a rate of 219 g/hr. Sodium hydroxide as the catalyst was dissolved in the recycled part of the reaction mixture to give a 2% solution and this solution was fed through line 8 to a position 150 mm below the top at a rate of 90 g/hr. While keeping the inner temperature of the still at 120° C. and continuously operating the apparatus under normal pressure at a reflux ratio of 0, the distillate was taken out through line 7 at a rate of 361 g/hr on the one hand, and the bottom stream was taken out through line 9 at a rate of 192 g/hr on the other hand. From the bottom stream, 1,4-butanediol having a purity of 99% or more was obtained by a simple distillation at a rate of 171 g/hr. The molar ratio of tetrahydrofuran to 1,4-butanediol, thus obtained, was 35/65.

In this experiment, the chemical compositions at principal locations were as follows, wherein the locations are expressed in accordance with the numerical symbols used in the accompanying drawings:

| 4 | Tetrahydrofuran | 29.2 mole % |
|---|---|---|
|   | Water | 7.5 mole % |
|   | Acetic acid | 63.3 mole % |
| 5 | 1,4-Diacetoxybutane | 90.8 mole % |
|   | 1-Hydroxy-4-acetoxybutane | 9.2 mole % |
|   | 1,4-Butanediol | Trace |
| 7 | Methyl acetate | 57.5 mole % |
|   | Methanol | 42.5 mole % |
| 9 | Methanol | 16.7 mole % |
|   | 1-Hydroxy-4-actoxybutane | 0.8 mole % |
|   | 1,4-Butanediol | 82.5 mole % |

COMPARATIVE EXAMPLE

The transesterification of Example 1 was repeated, except that pure 1,4-diacetoxybutane was substituted for the bottom stream withdrawn from the first distillation column.

1,4-Diacetoxybutane was fed to a position 100 mm below the top of the second distillation column in the same molar amount (339 g/hr) as the bottom stream of the first distillation column. Methanol was fed to a position 400 mm above the bottom of the reaction-distillation column at the same rate as in Example 1 (219 g/hr). Sodium hydroxide as the catalyst was dissolved in the recycled part of the reaction mixture to form a 4% solution (twice the concentration in Example 1) and this solution was fed to a position 150 mm below the top at a rate of 90 g/hr.

While operating the apparatus in the same manner as in Example 1, the distillate was taken out through line 7 at a rate of 365 g/hr, while the bottom stream was taken out through line 9 at a rate of 197 g/hr. From the bottom stream, 1,4-butanediol having a purity of 94.8 mole% was obtained at a rate of 174 g/hr by the same distillation as in Example 1. The remainder was unreacted 1-hydroxy-4-acetoxybutane. That is to say, due to the insufficient supply of methanol, there was obtained only 1,4-butanediol having a low purity in spite of an increased amount of catalyst.

In the same manner as in Example 1, the chemical compositions at the principal locations are shown below in accordance with the numerical symbols used in the accompanying drawing.

| 7 | Methyl acetate | 58.7 mole % |
|---|---|---|
|   | Methanol | 41.3 mole % |
| 9 | Methyl acetate | 0.9 mole % |
|   | Methanol | 15.8 mole % |
|   | 1-Hydroxy-4-acetoxybutane | 4.3 mole % |
|   | 1,4-Butanediol | 79.1 mole % |

EXAMPLE 2

The same procedure as in Example 1 was repeated in the same apparatus as in Example 1, except that a part of the bottom stream from the first distillation column was circulated to the reactor to subject it to cyclization, simultaneously with which methanol containing methyl acetate was used as the starting methanol for the transesterification, to conduct the continuous operation of the apparatus.

To the reactor were fed water at a rate of 36 g/hr through line 1, 1,4-diacetoxybutane at a rate of 522 g/hr through line 2 and a part of the bottom stream from the first distillation column at a rate of 179 g/hr, said bottom stream having been taken out through line 5 and containing 1-hydroxy-4-acetoxybutane, and reaction was effected under the same conditions as in Example 1.

The reaction mixture was taken out through line 3 and fed to the first distillation column, and a distillate was taken out at a rate of 289 g/hr through line 4. This distillate was purified by distillation to obtain tetrahydrofuran with a purity of 99.9% or more at a rate of 101 g/hr.

On the other hand, the remainder of the bottom stream from the first distillation column was fed to a position 100 mm below the top of the second reaction-distillation column at a rate of 269 g/hr and methanol containing 20 mole% of methyl acetate was fed to a position 400 mm above the bottom of the second reaction-distillation column at a rate of 319 g/hr. Sodium hydroxide as the catalyst was dissolved in a part of the reaction mixture taken out from the bottom of the column to form a 2% solution and this solution was fed to a position 150 mm below the top of the second reaction-distillation column at a rate of 73 g/hr as in Example 1.

The apparatus was operated continuously as in Example 1 while taking out a distillate at a rate of 435 g/hr through line 7 and a bottom stream at a rate of 153 g/hr through line 9. The bottom stream was purified by simple distillation to obtain 1,4-butanediol with a purity of 99% or more at a rate of 139 g/hr.

The molar ratio of the tetrahydrofuran obtained to the 1,4-butanediol obtained was 48/52. The chemical compositions at principal locations in this experiment were as follows, in which the locations are expressed in accordance with the numerical symbols used in the accompanying drawing:

| 4 | Tetrahydrofuran | 29.5 mole % |
|---|---|---|
| | Water | 8.6 mole % |
| | Acetic acid | 61.9 mole % |
| 5 | 1,4-Diacetoxybutane | 90.8 mole % |
| | 1-Hydroxy-4-acetoxybutane | 9.2 mole % |
| | 1,4-Butanediol | trace |
| 7 | Methyl acetate | 60.4 mole % |
| | Methanol | 39.6 mole % |
| 9 | Methanol | 16.7 mole % |
| | 1-Hydroxy-4-acetoxybutane | 0.8 mole % |
| | 1,4-Butanediol | 82.5 mole % |

What is claimed is:

1. A process for producing simultaneously tetrahydrofuran and 1,4-butanediol at any desired proportion which comprises (a) reacting the diacetic ester of 1,4-butanediol with a theoretical or smaller quantity, based on said diacetic ester, of water in the presence of an acidic catalyst, (b) separating, in a first distillation column, the reaction mixture obtained into a distillate comprising tetrahydrofuran as major constituent and a bottom stream comprising the diacetic ester of 1,4-butanediol as major constituent, and (c) subjecting, in the second reaction-distillation column, at least a part of said bottom stream to a counter-current gas-liquid contact reaction with methanol in the presence of an acidic or basic catalyst and separating the reaction mixture into a bottom stream comprising 1,4-butanediol as major constituent and a distillate comprising methyl acetate as major constituent.

2. A process according to claim 1, wherein the amount of water in step (a) is 0.2–0.8 mole per mole of the diacetic ester.

3. A process according to claim 1, wherein the methanol in step (c) is a mixture consisting of 20 mole% or more of methanol and 80 mole% or less of methyl acetate.

4. A process according to claim 1, wherein the methanol in step (c) is a mixture consisting of 40 mole% or more of methanol and 60 mole% or less of methyl acetate.

5. A process according to claim 3, wherein the amount of methanol is 1–5 moles per mole of the ester group of the acetic ester of 1,4-butanediol in the bottom stream.

6. A process according to claim 4, wherein the amount of methanol is 1–5 moles per mole of the ester group of the acetic ester of 1,4-butanediol in the bottom stream.

7. A process according to claim 1, wherein the starting diacetic ester of 1,4-butanediol in step (a) is 1,4-diacetoxybutane.

8. A process according to claim 6, wherein the starting diacetic ester of 1,4-butanediol in step (a) is 1,4-diacetoxybutane.

9. A process according to claim 1, wherein the acidic catalyst in step (a) is a member selected from the group consisting of sulfuric acid, phosphoric acid, an acidic cation exchange resin, solid phosphoric acid and silica-alumina.

10. A process according to claim 1, wherein the catalyst in step (c) is an acidic catalyst selected from the group consisting of sulfuric acid, phosphoric acid, an acidic cation exchange resin, solid phosphoric acid and silica-alumina.

11. A process according to claim 1, wherein the catalyst in step (c) is a basic catalyst selected from the group consisting of sodium hydroxide, potassium hydroxide, sodium alkoxide, aluminium alkoxide and ammonia.

12. A process according to claim 1, wherein the starting diacetic ester of 1,4-butanediol in step (a) contains 50 mole percent or less of the monoacetic ester of 1,4-butanediol.

13. A process according to claim 2, wherein the methanol in step (c) is a mixture consisting of 20 mole% or more of methanol and 80 mole% or less of methyl acetate.

14. A process according to claim 2, wherein the methanol in step (c) is a mixture consisting of 40 mole% or more of methanol and 60 mole% or less of methyl acetate.

15. A process according to claim 2, wherein the starting diacetic ester of 1,4-butanediol in step (a) is 1,4-diacetoxybutane.

* * * * *